United States Patent
Yu et al.

(10) Patent No.: US 11,253,228 B2
(45) Date of Patent: Feb. 22, 2022

(54) ULTRASONIC SCANNING METHOD AND ULTRASONIC SCANNING DEVICE

(71) Applicant: Acer Incorporated, New Taipei (TW)

(72) Inventors: Chun-Hsien Yu, New Taipei (TW); Kuo-Nan Chen, New Taipei (TW)

(73) Assignee: Acer Incorporated, New Taipei (TW)

( * ) Notice: Subject to any disclaimer, the term of this patent is extended or adjusted under 35 U.S.C. 154(b) by 204 days.

(21) Appl. No.: 16/409,867

(22) Filed: May 13, 2019

(65) Prior Publication Data

US 2020/0214671 A1 Jul. 9, 2020

(30) Foreign Application Priority Data

Jan. 4, 2019 (TW) .................... 108100344

(51) Int. Cl.
*A61B 8/00* (2006.01)
*A61B 8/08* (2006.01)

(52) U.S. Cl.
CPC ............ *A61B 8/4461* (2013.01); *A61B 8/483* (2013.01); *A61B 8/5207* (2013.01); *A61B 8/58* (2013.01); *A61B 8/4483* (2013.01)

(58) Field of Classification Search
CPC ......... A61B 8/4461; A61B 8/483; A61B 8/58; A61B 8/5207; A61B 8/4483; A61B 8/5223; A61B 8/5292; A61B 8/54; G06T 7/0014; G06K 9/6261; G06K 9/00
See application file for complete search history.

(56) References Cited

U.S. PATENT DOCUMENTS

| | | | |
|---|---|---|---|
| 2013/0331697 A1* | 12/2013 | Park | A61B 8/523 600/440 |
| 2015/0182191 A1* | 7/2015 | Caluser | A61B 5/4312 600/440 |
| 2015/0216512 A1 | 8/2015 | Luo et al. | |
| 2017/0360401 A1* | 12/2017 | Rothberg | A61B 8/46 |
| 2018/0310920 A1* | 11/2018 | Specht | A61B 8/5207 |
| 2019/0216437 A1* | 7/2019 | Yamada | A61B 8/5246 |
| 2020/0069285 A1* | 3/2020 | Annangi | A61B 8/54 |

FOREIGN PATENT DOCUMENTS

| | | |
|---|---|---|
| CN | 103327905 | 9/2013 |
| EP | WO 2015075612 A1 * | 5/2015 |
| TW | 201800057 | 1/2018 |
| WO | 2015075612 | 5/2015 |

* cited by examiner

*Primary Examiner* — Joseph M Santos Rodriguez
*Assistant Examiner* — Kaitlyn E Selmer
(74) *Attorney, Agent, or Firm* — JCIPRNET

(57) ABSTRACT

An ultrasonic scanning method for an ultrasonic scanning device is provided according to an embodiment of the disclosure. The ultrasonic scanning method includes: performing an ultrasonic scanning operation on a human body by an ultrasonic scanner to obtain an ultrasonic image; analyzing the ultrasonic image by an image recognition module to identify an organ pattern in the ultrasonic image; and generating, automatically, a guiding message according to an identification result of the organ pattern, wherein the guiding message is configured to guide a moving of the ultrasonic scanner to scan a target organ of the human body.

6 Claims, 5 Drawing Sheets

| Images | Coordinates |
|---|---|
| 1 | (x1,y1) |
| 2 | (x2,y2) |
| 3 | (x3,y3) |
| 4 | (x4,y4) |
| 5 | (x5,y5) |

ULTRASONIC SCANNING METHOD AND ULTRASONIC SCANNING DEVICE

CROSS-REFERENCE TO RELATED APPLICATION

This application claims the priority benefit of Taiwan application serial no. 108100344, filed on Jan. 4, 2019. The entirety of the above-mentioned patent application is hereby incorporated by reference herein and made a part of this specification.

BACKGROUND

Technical Field

The disclosure is related an ultrasonic scanning technology, and more particularly related to an ultrasonic scanning method and an ultrasonic scanning device.

Description of Related Art

The ultrasonic scanning device may be used to obtain an organ image of a human body based on ultrasonic waves to evaluate an organ state based on the organ image. However, conventional ultrasonic scanning devices require professional operation, and ultrasonic images obtained by ultrasonic scanning also require professional identification. It is not easy for a person without professional training to identify a particular organ from the ultrasonic images. Furthermore, in practice, professionals such as doctors or inspectors may also misinterpret organ patterns due to various conditions (such as lack of professionalism or fatigue) when operating an ultrasonic scanning device, which leads to inefficiency in the inspection and even to inaccurate inspection results.

SUMMARY

The disclosure provides an ultrasonic scanning method and an ultrasonic scanning device, which may automatically analyze ultrasonic images and provide a guiding message for assisting scanning according to the analysis result, thereby improving the above problem.

An ultrasonic scanning method for an ultrasonic scanning device is provided according to an embodiment of the disclosure. The ultrasonic scanning method includes: performing an ultrasonic scanning operation on a human body by an ultrasonic scanner to obtain an ultrasonic image; analyzing the ultrasonic image by an image recognition module to identify an organ pattern in the ultrasonic image; and generating, automatically, a guiding message according to an identification result of the organ pattern, wherein the guiding message is configured to guide a moving of the ultrasonic scanner to scan a target organ of the human body.

An ultrasonic scanning device including an ultrasonic scanner and a processor is provided according to an embodiment of the disclosure. The ultrasonic scanner is configured to perform an ultrasonic scanning operation on a human body to obtain an ultrasonic image. The processor is coupled to the ultrasonic scanner and configured to analyze the ultrasonic image by an image recognition module to identify an organ pattern in the ultrasonic image. The processor is further configured to generate, automatically, a guiding message according to an identification result of the organ pattern, and the guiding message is configured to guide a moving of the ultrasonic scanner to scan a target organ of the human body.

Based on the above, after performing an ultrasonic scanning operation on the human body via the ultrasonic scanner to obtain an ultrasonic image, the image recognition module may analyze the ultrasonic image to identify an organ pattern in the ultrasonic image. Then, the guiding message may be automatically generated according to the identification result of the organ pattern. In particular, the guiding message may direct the movement of the ultrasonic scanner to scan the target organ of the human body, thereby reducing the burden on professionals to perform the ultrasonic scanning and/or unsupervised personnel may also easily operate the ultrasonic scanning device for simple scanning.

To make the aforementioned more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

DESCRIPTION OF THE EMBODIMENTS

Figure 1:
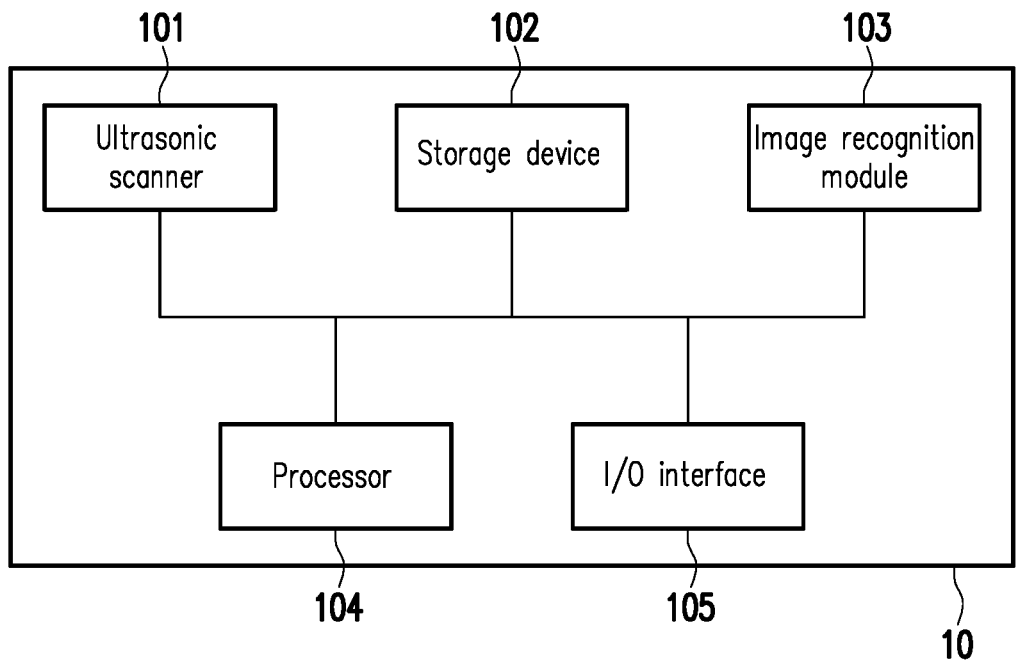
FIG. 1 is a schematic diagram of an ultrasonic scanning device according to an embodiment of the disclosure.

FIG. 1 is a schematic diagram of an ultrasonic scanning apparatus according to an embodiment of the disclosure. Referring to FIG. 1, the ultrasonic scanning device 10 includes an ultrasonic scanner 101, a storage device 102, an image recognition module 103, a processor 104, and an input/output (I/O) interface 105. The ultrasonic scanner 101 is configured to perform an ultrasonic scanning operation on a human body to obtain ultrasonic images. For example, the ultrasonic scanner 101 may include a hand-held probe. The ultrasonic scanner 101 may emit ultrasonic waves and receive ultrasonic waves reflected from a human organ. The ultrasonic images may be obtained based on the reflected ultrasonic waves. In the following embodiments, two-dimensional ultrasonic images are taken as examples for description. However, in another embodiment, the ultrasonic image may also include three-dimensional ultrasonic images, which is not limited in the present disclosure.

The storage device 102 is used to store data. For example, the storage device 102 may include a volatile storage medium and a non-volatile storage medium. The volatile storage medium may include a random access memory (RAM). The non-volatile memory module may include a flash memory module, a read only memory (ROM), a solid state drive (SSD), and/or a conventional hard disk (e.g., a hard disk drive, HDD), etc. In addition, the number of storage devices 102 may be one or more, which is not limited by the disclosure.

The image recognition module 103 is configured to perform an image recognition on the obtained ultrasonic image. For example, the image recognition module 103 may perform the image recognition based on a convolutional neural network (CNN) architecture or other type of image recognition architecture (or algorithm). The image recognition module 103 may be implemented in a software or hardware form. In an embodiment, the image recognition module 103 includes a software module. For example, the code of the image recognition module 103 may be stored in the storage device 102 and may be executed by the processor 104. In an embodiment, the image recognition module 103 includes a hardware circuit. For example, the image recognition module 103 may include a graphics processing unit (GPU) or other programmable general purpose or special purpose microprocessor, a digital signal processor, a programmable controller, a special application integrated circuit, programmable logic devices or other similar devices or a combination of these devices. In addition, the number of the image recognition modules 103 may be one or more, which is not limited by the present disclosure.

The processor 104 is coupled to the ultrasonic scanner 101, the storage device 102, and the image recognition module 103. The processor 104 may be used to control the ultrasonic scanner 101, the storage device 102, and the image recognition module 103. For example, the processor 104 may include a central processing unit (CPU), a graphics processor, or other programmable general purpose or special purpose microprocessor, a digital signal processor, a programmable controller, a special application integrated circuit, programmable logic devices or other similar devices or a combination of these devices. In an embodiment, the processor 104 may be used to control the overall or partial operation of the ultrasonic scanning device 10. In an embodiment, the image recognition module 103 may be implemented inside the processor 104 in a software, a firmware or a hardware form. Moreover, the number of processors 104 may be one or more, and the disclosure is not limited thereto.

The I/O interface 105 is coupled to the processor 104. The I/O interface 105 is configured to receive signals and/or output signals. For example, the I/O interface 105 may include a screen, a touch screen, a touch pad, a mouse, a keyboard, a physical button, a speaker, a microphone, a wired communication interface, and/or a wireless communication interface, and the type of the I/O interface 105 is not limited thereto.

Figure 2:
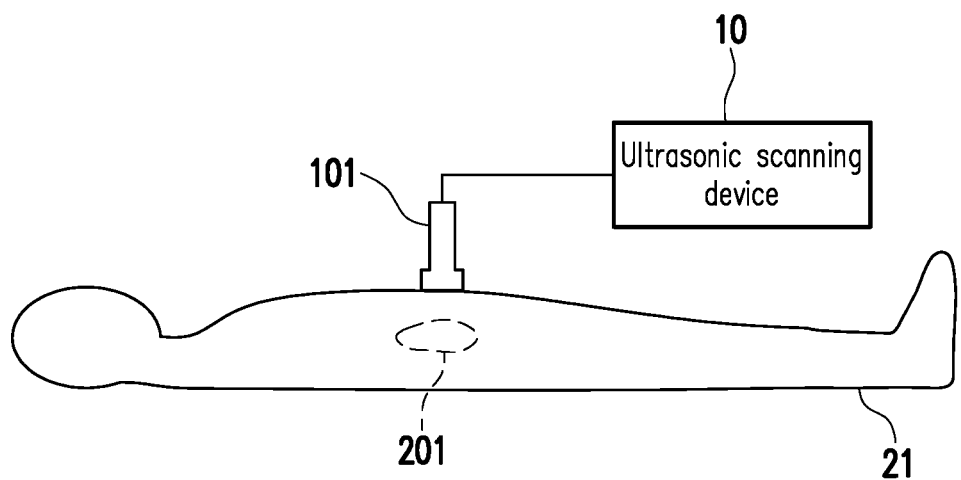
FIG. 2 is a schematic diagram of an ultrasonic scanning operation according to an embodiment of the disclosure.

FIG. 2 is a schematic diagram of an ultrasonic scanning operation according to an embodiment of the disclosure. Referring to FIG. 1 and FIG. 2, an operator may hold the ultrasonic scanner 101 and move the ultrasonic scanner 101 on the human body 21 to perform an ultrasonic scanning operation. Further, a gel may be applied between the ultrasonic scanner 101 and the human body 21 to facilitate the ultrasonic scanning operation. Taking FIG. 2 as an example, the ultrasonic images obtained by this ultrasonic scanning operation may present a pattern (also referred to as an organ pattern) of an organ 201. For example, the organ 201 may include various human organs such as the heart, the liver, and/or the uterus, and the present disclosure is not limited thereto. The obtained ultrasonic images may be stored in the storage device 102.

The processor 104 may analyze the ultrasonic images by the image recognition module 103 to identify an organ pattern in the ultrasonic images. The processor 104 may automatically generate a guiding message according to the identification result of the organ pattern. This guiding message may be used to guide the movement (or moving) of the ultrasonic scanner 101 to scan a specific organ (also referred to as a target organ) of the human body 21. For example, the guiding message may be output as an image by a screen of the I/O interface 105 and/or as a sound by a speaker of the I/O interface 105. Alternatively, the guiding message may also be output in other forms (such as a vibrating or buzzer), which is not limited by the disclosure. Further, the target organ may be various human organs such as the heart, the liver, and/or the uterus, and the present disclosure is not limited thereto. The operator may move the ultrasonic scanner 101 according to the guiding message to continuously scan the target organ and/or continuously enlarge the pattern area of the target organ in the ultrasonic images during the scanning process.

In an embodiment, the guiding message may include a direction message. The operator may move the ultrasonic scanner 101 in a specific direction according to the guiding message. In an embodiment, the guiding message may include a message indicating whether the current direction of movement of the ultrasonic scanner 101 is correct. The operator may determine whether to change the moving direction of the ultrasonic scanner 101 based on the guiding message. In this way, even if the operator is not trained in professional ultrasonic scanning and/or in analysis of the ultrasonic images, one general user may also perform an ultrasonic scanning of the target organ based on the guiding message and/or obtain an ultrasonic image showing the complete pattern (or maximum pattern area) of the target organ. In addition, the guiding message may also be used to guide a professional such as a doctor or an inspector to assist in the ultrasonic scanning of the target organ.

In an embodiment, the processor 104 may record coordinate information corresponding to a certain ultrasonic image. This coordinate information may reflect the position of the ultrasonic scanner 101 when capturing (or obtaining) the ultrasonic image. For example, a sensor module may be disposed in the ultrasonic scanner 101. For example, the sensor module may include an optical sensor, a gyroscope, and a gravity sensor (e.g., G-sensor) to sense a position, a moving direction, and/or a moving distance of the ultrasonic scanner 101. The processor 104 may obtain the coordinate information corresponding to a certain ultrasonic image according to the information provided by the sensor module.

Figures 3, 4:
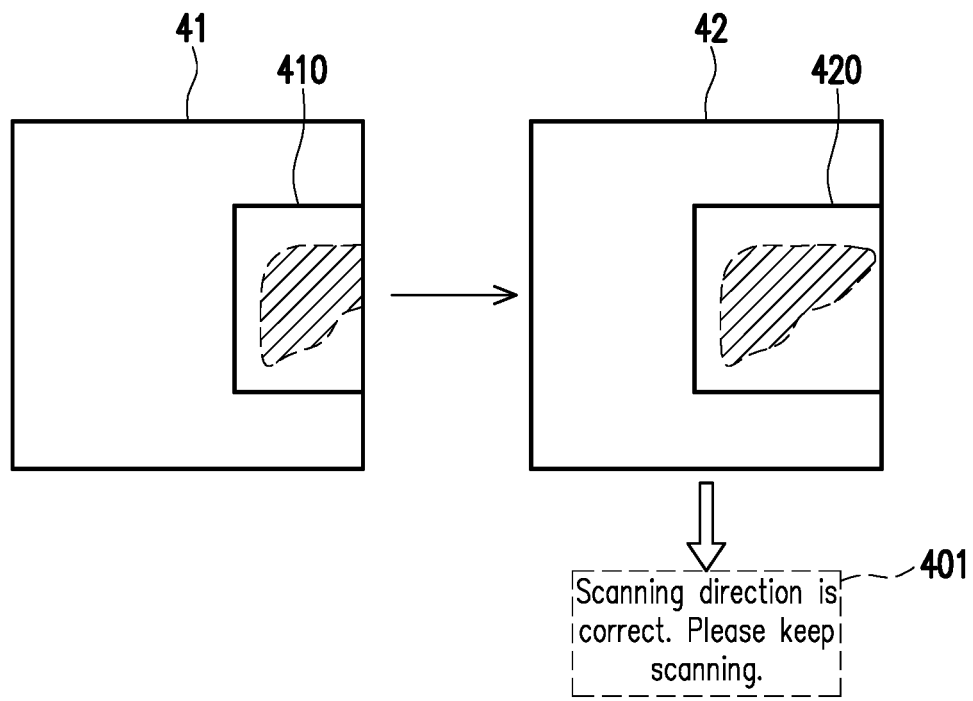
FIG. 3 is a schematic diagram of ultrasonic images and corresponding coordinate information according to an embodiment of the disclosure.
FIG. 4 and FIG. 5 are schematic diagrams showing guiding messages according to a numerical relationship between areas of prediction blocks according to an embodiment of the disclosure.

FIG. 3 is a schematic diagram of ultrasonic images and corresponding coordinate information according to an embodiment of the disclosure. Referring to FIG. 3, coordinate table 31 records a plurality of coordinates (x1, y1) to (x5, y5) corresponding to the ultrasonic images numbered 1 to 5. Taking the ultrasonic images numbered 1 and 2 as an example, when capturing the ultrasonic image numbered 1, the position of the ultrasonic scanner 101 is at a coordinate (x1, y1); when capturing an ultrasonic image numbered 2, the position of the ultrasonic scanner 101 is at a coordinate (x2, y2), and so on. After performing image recognition of the organ pattern on a certain ultrasonic image, the processor 104 may generate the guiding message according to the identification result of the organ pattern and the coordinate information corresponding to the ultrasonic images in the coordinate table 31. In other words, the current position, the past positions, and/or movement trajectory of the ultrasonic scanner 101 may be considered in the operation of generating the guiding message. It should be noted that the five ultrasonic images in the coordinate table 31 are merely examples. In another embodiment, more or fewer ultrasonic images and the corresponding coordinate information may be recorded in the coordinate table 31. Alternatively, the coordinate table 31 may also record the ultrasonic images and the corresponding coordinate information in other forms. In addition, more information that may be used to generate the guiding message may also be recorded in the coordinate table 31, depending on actual needs.

In an embodiment, the image recognition module 103 may determine a prediction block in an ultrasonic image. The prediction block reflects a range of the organ pattern recognized by the image recognition module 103 in the ultrasonic image. Taking an ultrasonic image including a liver pattern as an example, after performing an image recognition on the ultrasonic image, the image recognition module 103 may determine a prediction block in the ultrasonic image. This prediction block reflects the approximate range of the liver pattern in this ultrasonic image.

In an embodiment, the prediction block covers a range of the organ pattern of the target organ. For example, if a plurality of organ patterns are included in one ultrasonic image, the image recognition module 103 may determine a prediction block according to an organ pattern (also referred to as a target organ pattern) belonging to the target organ among the organ patterns, so that the prediction block may (only) cover the range of this target organ pattern. From another point of view, after determining the target organ, the image recognition module 103 may start tracking the organ pattern of the target organ and ignore the remaining organ patterns that do not belong to the target organ. For example, assuming that the determined target organ is the liver, the image recognition module 103 may begin tracking the liver pattern that may appear in the ultrasonic images and ignore the organ patterns of the remaining organs (e.g., kidney or heart) in the ultrasonic images.

In an embodiment, the processor 104 may obtain an area of the prediction block in a certain ultrasonic image. The size of this area may reflect the proportion of the area occupied by the prediction block in the ultrasonic image. The processor 104 may generate the guiding message based on the area. For example, after continuously obtaining a plurality of ultrasonic images, the processor 104 may generate the guiding message according to a numerical relationship between the areas of the prediction blocks in these ultrasonic images. For example, the numerical relationship may reflect the change in areas between such prediction blocks.

Figure 5:
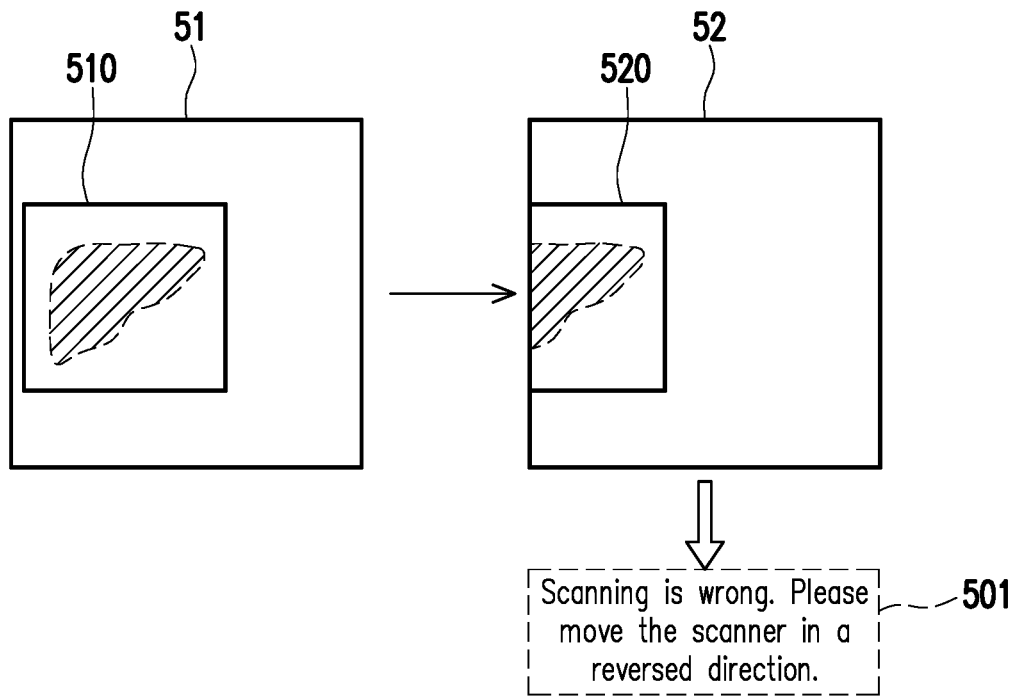

FIG. 4 and FIG. 5 are schematic diagrams showing guiding messages according to a numerical relationship between areas of prediction blocks according to an embodiment of the disclosure. Referring to FIG. 4, it is assumed that after an ultrasonic image 41 is obtained, an ultrasonic image 42 is successively obtained by moving the ultrasonic scanner 101. The prediction block 410 in the ultrasonic image 41 is determined, and the prediction block 420 in the ultrasonic image 42 is determined. The prediction blocks 410 and 420 may respectively cover at least a portion of the organ pattern of the target organ (marked with diagonal lines in FIG. 4).

The processor 104 may compare the area of the prediction block 410 to the area of the prediction block 420 to obtain a numerical relationship between the areas of prediction blocks 410 and 420. In the present embodiment, the numerical relationship between the areas of the prediction blocks 410 and 420 reflects that the area of the prediction block 410 is smaller than the area of the prediction block 420. Accordingly, the processor 104 may generate a guiding message (also referred to as a first guiding message) 401 to indicate the operator of the ultrasonic scanner 101 that the current scanning direction is correct and the scanning can continue.

In an embodiment, the area of the prediction block 410 being smaller than the area of the prediction block 420 may be considered as a first numerical relationship between the prediction blocks 410 and 420. The first numerical relationship indicates that as the ultrasonic scanner 101 moves, the areas of the prediction blocks in the ultrasonic images gradually increases (equivalent to the areas of the patterns of the target organ in the ultrasonic images gradually increases), as shown in FIG. 4. Therefore, the guiding message 401 may inform the operator to continue the scanning based on the current moving direction of the ultrasonic scanner 101 without adjusting the moving direction of the ultrasonic scanner 101. Thereby, the scanning position of the ultrasonic scanner 101 may be gradually brought closer to the position of the target organ.

Referring to FIG. 5, it is assumed that after an ultrasonic image 51 is obtained, an ultrasonic image 52 is successively obtained by moving the ultrasonic scanner 101. The prediction block 510 in the ultrasonic image 51 is determined, and the prediction block 520 in the ultrasonic image 52 is determined. The prediction blocks 510 and 520 may respectively cover at least a portion of the organ pattern of the target organ (marked with diagonal lines in FIG. 5).

The processor 104 may compare the area of the prediction block 510 with the area of the prediction block 520 to obtain a numerical relationship between the areas of the prediction blocks 510 and 520. In the present embodiment, the numerical relationship between the areas of the prediction blocks 510 and 520 reflects that the area of the prediction block 510 is larger than the area of the prediction block 520. Therefore, the processor 104 may generate a guiding message (also referred to as a second guiding message) 501 to remind the operator of the ultrasonic scanner 101 that the current scanning direction is wrong and the ultrasonic scanner 101 may be moved in the opposite (or reversed) direction (or other directions).

In an embodiment, the area of the prediction block 510 being greater than the prediction block 520 may be considered as the second numerical relationship between the prediction blocks 510 and 520. The second numerical relationship indicates that as the ultrasonic scanner 101 moves, the areas of the prediction blocks in the ultrasonic images are gradually reduced (equivalent to the areas of the patterns of the target organ in the ultrasonic images gradually decreasing), as shown in FIG. 5. Therefore, the guiding message 501 may suggest the operator to change the moving direction of the ultrasonic scanner 101. Thereby, the scanning positions of the ultrasonic scanner 101 being kept away from the position of the target organ may be avoided. In an embodiment, the guiding messages 401 and/or 501 may be generated with reference to the coordinate table 31 of FIG. 3 to obtain the previous direction of movement of the ultrasonic scanner 101 and provide a suggested direction of a next movement.

In one embodiment, the processor 104 may continuously record the areas of the predicted blocks in the plurality of ultrasonic images. Based on the comparison result of the areas of the prediction blocks, the processor 104 may obtain particular coordinate information (also referred to as target coordinate information). The target coordinate information corresponds to one of the ultrasonic images (also referred to as a target image). The prediction block in the target image has the largest covering range relative to the other prediction blocks in the remaining ultrasonic images. For example, if the target image is the ultrasonic image numbered 3 in FIG. 3, then the target coordinate information is (x3, y3), and the area of the prediction block in the ultrasonic image numbered 3 is larger than the area of the prediction block in any one of the ultrasonic images numbered 1, 2, 4 and 5.

In an embodiment, the processor 104 may generate a guiding message (also referred to as a third guiding message) according to the target coordinate information. For example, the processor 104 may generate the third guiding message according to the target coordinate information and the current position of the ultrasonic scanner 101. The third guiding message may be used to assist the operator in moving of the ultrasonic scanner 101 to a scanning position corresponding to the target coordinate information. After the ultrasonic scanner 101 is moved to the scanning position corresponding to the target coordinate information, the ultrasonic image having the largest prediction block (equivalent to the largest organ pattern of the target organ) (e.g., the ultrasonic image 42 of FIG. 4 or the ultrasonic image 51 of FIG. 5) may be obtained again. In other words, in an embodiment, the third guiding message may be used to guide the ultrasonic scanner 101 to a scanning position at which the largest organ pattern of the target organ is obtained.

Figure 6:
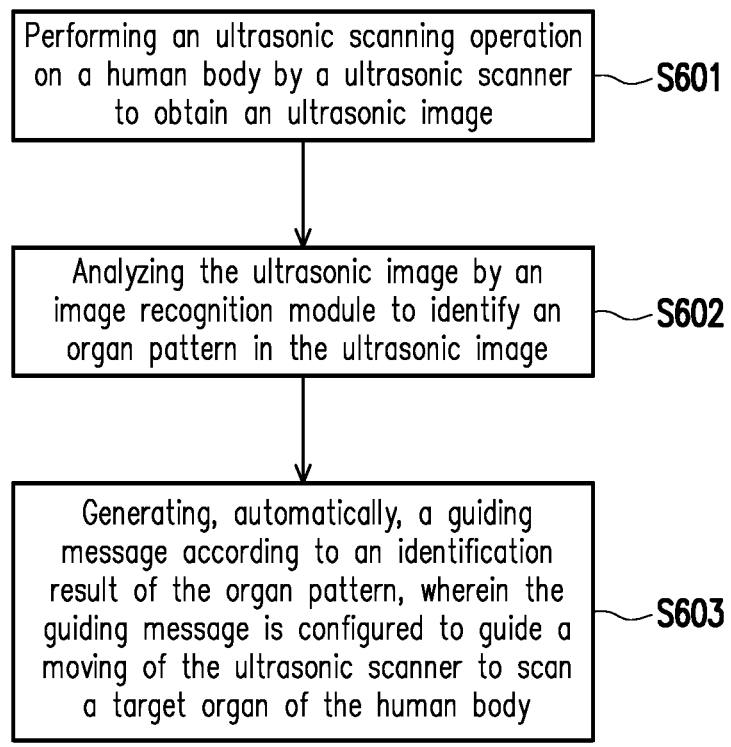
FIG. 6 is a flow chart of an ultrasonic scanning method according to an embodiment of the disclosure.

FIG. 6 is a flow chart of an ultrasonic scanning method according to an embodiment of the disclosure. Referring to FIG. 6, in step S601, an ultrasonic scanning operation is performed on the human body by an ultrasonic scanner to obtain an ultrasonic image. In step S602, the ultrasonic image is analyzed by an image recognition module to recognize an organ pattern in the ultrasonic image. In step S603, a guiding message is automatically generated according to the identification result of the organ pattern. The guiding message is used to guide the movement of the ultrasonic scanner to scan a target organ of the human body.

Figure 7:
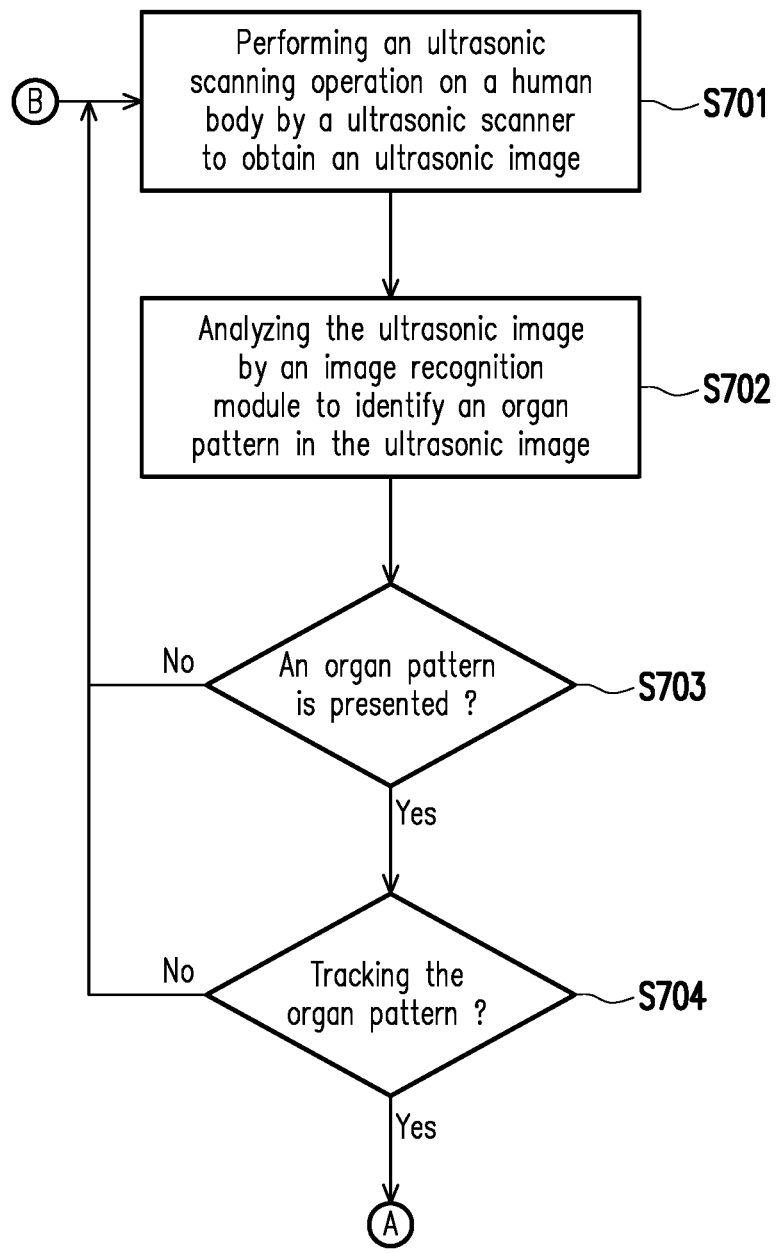
FIG. 7 and FIG. 8 are flow charts of an ultrasonic scanning method according to an embodiment of the disclosure.
Figure 8:
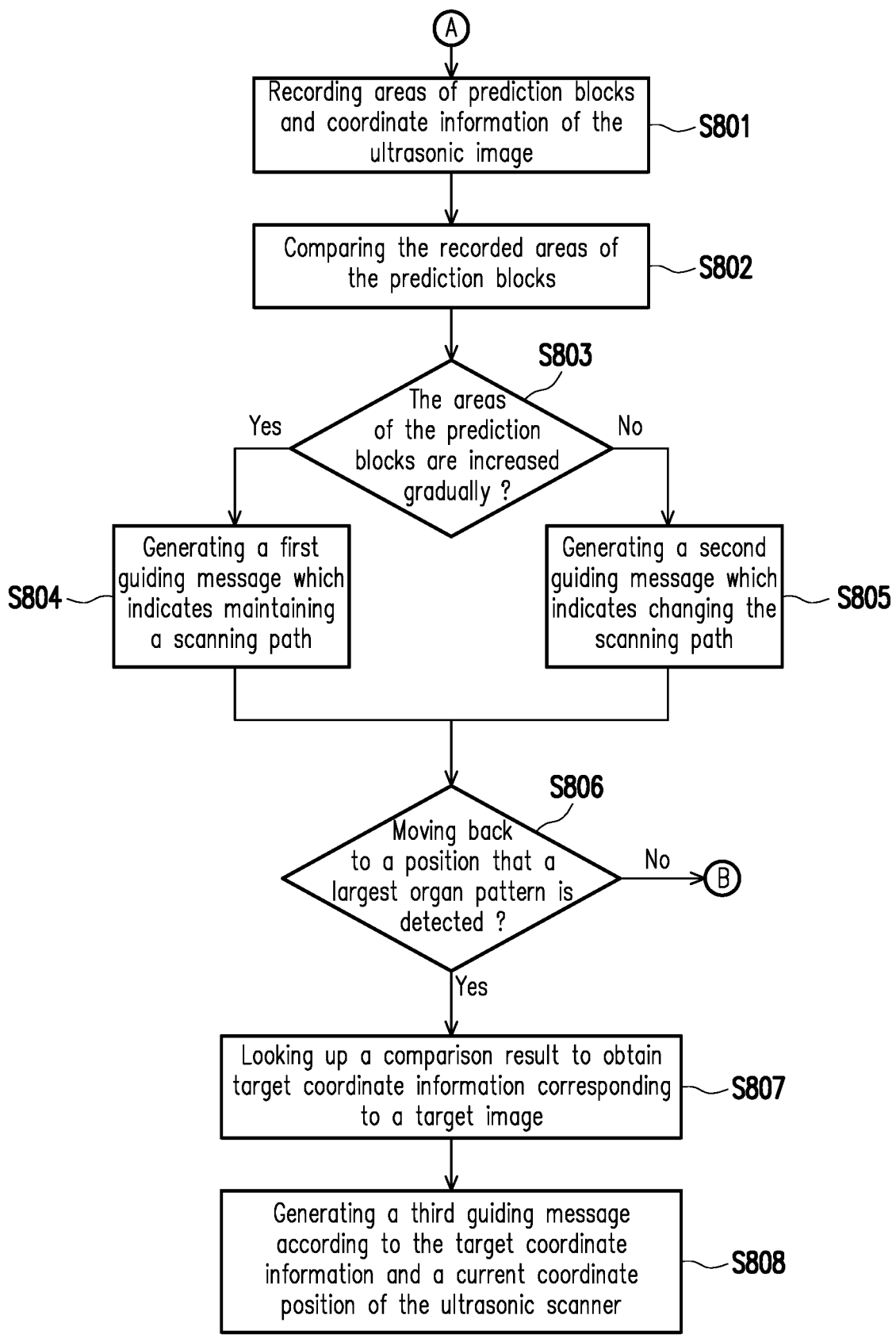

FIG. 7 and FIG. 8 are flow charts of an ultrasonic scanning method according to an embodiment of the disclosure. Referring to FIG. 7, in step S701, an ultrasonic scanning operation is performed on the human body by an ultrasonic scanner to obtain an ultrasonic image. In step S702, the ultrasonic image is analyzed by an image recognition module to recognize an organ pattern in the ultrasonic image. In step S703, it is determined whether or not an organ pattern appears in the ultrasonic images. If the organ pattern does not appear in the ultrasonic images, the method returns back to the step S701. If the organ pattern appears in the ultrasonic image, it is determined in step S704 whether to track the organ pattern. For example, in step S704, whether to track the organ pattern may be determined according to a user operation. If it is determined to track the organ pattern, it means that the current organ pattern is the organ pattern of the target organ and the method goes to step S801 of FIG. 8 to start tracking. On the other hand, if the organ pattern is not tracked, it means that the operator may not yet move the ultrasonic scanner to the scanning position covering the organ pattern of the target organ, so step S701 may be repeated.

Referring to FIG. 8, in step S801, the areas of the prediction blocks in the ultrasonic images and the coordinate information of the ultrasonic images are recorded. In step S802, the areas of the plurality of prediction blocks are compared. In step S803, it is determined whether the areas of the prediction blocks in the ultrasonic images are gradually increased. If the areas of the prediction blocks in the ultrasonic images are gradually increased, in step S804, a first guiding message indicating maintaining the scanning path (or the scanning direction is correct) is generated. Alternatively, if the areas of the prediction blocks in the ultrasonic images are not gradually increased (e.g., gradually decreased), then in step S805, a second guiding message indicating changing the scanning path (or the scanning direction is wrong) is generated. After the steps S804 and S805, step S806 may be performed. In addition, in another embodiment, the step S806 may also be performed at any time point, and the present disclosure is not limited thereto.

In the step S806, it is determined, based on a user operation, whether the operator wants to move the ultrasonic scanner back to a scanning position that the largest organ pattern is identified. If the user operation, which reflects that the operator wants to move the ultrasonic scanner back to the scanning position that the largest organ pattern is identified, is not received, the method returns to the step S701 of FIG. 7 to continue the scanning. In addition, if the user operation, which reflects that the operator wants to move the ultrasonic scanner back to the scanning position that the largest organ pattern is identified, is received, in step S807, the comparison result of the areas of the previously recorded prediction blocks is looked up to obtain target coordinate information corresponding to a target image. In step S808, a third guiding message is generated according to the target coordinate information and the current coordinate position of the ultrasonic scanner.

However, the steps in FIG. 6 to FIG. 8 have been described in detail above, and will not be described again here. It should be noted that the steps in FIG. 6 to FIG. 8 may be implemented as a plurality of codes or circuits, and the present disclosure is not limited thereto. In addition, the methods of FIG. 6 to FIG. 8 may be used in combination with the above embodiments, or may be used alone, and the disclosure is not limited thereto.

In summary, after performing an ultrasonic scanning operation on the human body by the ultrasonic scanner to obtain an ultrasonic image, the image recognition module may analyze the ultrasonic image to identify an organ pattern in the ultrasonic image. Then, the guiding message may be automatically generated according to the identification result of the organ pattern. In particular, the guiding message may direct the movement of the ultrasonic scanner to scan the target organ of the human body, thereby reducing the burden on professionals to perform the ultrasonic scanning and/or unsupervised personnel may also easily operate the ultrasonic scanning device for simple scanning.

It will be apparent to those skilled in the art that various modifications and variations may be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. An ultrasonic scanning method for an ultrasonic scanning device, comprising:
performing an ultrasonic scanning operation on a human body by an ultrasonic scanner to obtain a plurality of ultrasonic images, wherein the ultrasonic images comprises a first ultrasonic image and a second ultrasonic image;
analyzing the ultrasonic image to identify an organ pattern in the ultrasonic images;
determining a first prediction block in the first ultrasonic image and a second prediction block in the second ultrasonic image, wherein the first prediction block reflects a range of the organ pattern identified in the first ultrasonic image, and the second prediction block reflects a range of the organ pattern identified in the second ultrasonic image;

comparing an area of the first prediction block with an area of the second prediction block to obtain a numerical relationship between the area of the first prediction block and the area of the second prediction block; and generating a guiding message for enlarging a pattern area of a target organ according to the numerical relationship, wherein the guiding message is configured to guide a moving of the ultrasonic scanner to scan the target organ of the human body.

2. The ultrasonic scanning method of claim 1, wherein the step of generating the guiding message according to the numerical relationship further comprises:

generating the guiding message according to coordinate information, wherein the coordinate information reflects a position of the ultrasonic scanner when the ultrasonic image is obtained.

3. The ultrasonic scanning method of claim 1, wherein the step of generating the guiding message according to the numerical relationship comprises:

obtaining target coordinate information according to the numerical relationship, wherein the target coordinate information corresponds to a target image in the ultrasonic image; and generating the guiding message according to the target coordinate information.

4. An ultrasonic scanning device, comprising:

an ultrasonic scanner, configured to perform an ultrasonic scanning operation on a human body to obtain a plurality of ultrasonic images, wherein the ultrasonic images comprises a first ultrasonic image and a second ultrasonic image; and a processor, coupled to the ultrasonic scanner and configured to analyze the ultrasonic image to identify an organ pattern in the ultrasonic images, wherein the processor is further configured to determine a first prediction block in the first ultrasonic image and a second prediction block in the second ultrasonic image, wherein the first prediction block reflects a range of the organ pattern identified in the first ultrasonic image, and the second prediction block reflects a range of the organ pattern identified in the second ultrasonic image, wherein the processor is further configured to compare an area of the first prediction block with an area of the second prediction block to obtain a numerical relationship between the area of the first prediction block and the area of the second prediction block, wherein the processor is further configured to generate a guiding message for enlarging a pattern area of a target organ according to the numerical relationship, and the guiding message is configured to guide a moving of the ultrasonic scanner to scan the target organ of the human body.

5. The ultrasonic scanning device of claim 4, wherein the operation of generating the guiding message according to the numerical relationship by the processor further comprises:

generating the guiding message according to coordinate information, wherein the coordinate information reflects a position of the ultrasonic scanner when the ultrasonic image is obtained.

6. The ultrasonic scanning device of claim 4, wherein the operation of generating the guiding message according to the numerical relationship by the processor comprises:

obtaining target coordinate information according to the numerical relationship, wherein the target coordinate information corresponds to a target image in the ultrasonic image; and generating the guiding message according to the target coordinate information.

\* \* \* \* \*